US010085931B2

(12) United States Patent
Baghdadli et al.

(10) Patent No.: US 10,085,931 B2
(45) Date of Patent: *Oct. 2, 2018

(54) PROCESS FOR PROTECTING AND REPAIRING KERATIN FIBRES USING ANIONIC OXIDIZED POLYSACCHARIDES

(71) Applicant: L'OREAL, Paris (FR)

(72) Inventors: Nawel Baghdadli, Massy (FR); Gwenaelle Jegou, Saint-Michel-sur-Orge (FR); Michel Philippe, Wissous (FR); Laurent Gilbert, Fourqueux (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/383,993

(22) PCT Filed: Mar. 8, 2013

(86) PCT No.: PCT/EP2013/054720
§ 371 (c)(1),
(2) Date: Sep. 9, 2014

(87) PCT Pub. No.: WO2013/132062
PCT Pub. Date: Sep. 12, 2013

(65) Prior Publication Data
US 2015/0040936 A1  Feb. 12, 2015

Related U.S. Application Data

(60) Provisional application No. 61/642,602, filed on May 4, 2012.

(30) Foreign Application Priority Data

Mar. 9, 2012 (FR) ..................... 12 52149

(51) Int. Cl.
A61K 8/73 (2006.01)
A61Q 5/12 (2006.01)
A61Q 5/00 (2006.01)

(52) U.S. Cl.
CPC ............... A61K 8/73 (2013.01); A61Q 5/002 (2013.01); A61Q 5/004 (2013.01); A61Q 5/12 (2013.01); A61K 2800/805 (2013.01)

(58) Field of Classification Search
None
See application file for complete search history.

(56) References Cited

U.S. PATENT DOCUMENTS

| 3,724,092 | A | 4/1973 | McCleerey |
| 4,185,087 | A | 1/1980 | Morlino |
| 4,452,261 | A | 6/1984 | Bresak et al. |
| 4,717,727 | A | 1/1988 | Gunzler et al. |
| 4,770,873 | A | 9/1988 | Wolfram et al. |
| 5,004,748 | A | 4/1991 | Baader et al. |
| 5,046,516 | A | 9/1991 | Barradas |
| 5,143,926 | A | 9/1992 | Baader et al. |
| 5,356,909 | A | 10/1994 | Baader et al. |
| 5,618,523 | A | 4/1997 | Zysman et al. |
| 5,665,778 | A | 9/1997 | Semeria et al. |
| 5,773,611 | A | 6/1998 | Zysman et al. |
| 5,957,140 | A | 9/1999 | McGee |
| 5,959,127 | A | 9/1999 | Semeria et al. |
| 5,992,425 | A | 11/1999 | Teratani et al. |
| 6,110,450 | A | 8/2000 | Bergmann |
| 8,163,273 | B2 | 4/2012 | Devin-Baudoin et al. |
| 2002/0172653 | A1 | 11/2002 | Cannell et al. |
| 2002/0187117 | A1 | 12/2002 | Devin-Baudoin et al. |
| 2002/0193264 | A1 | 12/2002 | Cannell et al. |
| 2003/0223945 | A1 | 12/2003 | Dalko et al. |
| 2005/0013786 | A1 | 1/2005 | Sabbagh et al. |
| 2005/0227902 | A1 | 10/2005 | Erazo-Majewicz et al. |
| 2008/0226576 | A1 | 9/2008 | Benabdillah et al. |
| 2009/0044823 | A1* | 2/2009 | Overend et al. .............. 132/211 |
| 2009/0215837 | A1 | 8/2009 | Dalko et al. |
| 2010/0016886 | A1 | 1/2010 | Lu |
| 2010/0105741 | A1 | 4/2010 | Dalko et al. |
| 2010/0263683 | A1 | 10/2010 | Dutheil-Gouret et al. |
| 2011/0020258 | A1 | 1/2011 | Lorant |
| 2011/0150812 | A1 | 6/2011 | Mecca |
| 2011/0268681 | A1 | 11/2011 | Gonzalez et al. |
| 2013/0131095 | A1 | 5/2013 | Dalko et al. |
| 2014/0076346 | A1 | 3/2014 | Bourdin et al. |

FOREIGN PATENT DOCUMENTS

| EP | 0095238 | A2 | 11/1983 |
| EP | 0176741 | A1 | 4/1986 |
| EP | 0217635 | A2 | 4/1987 |
| EP | 0281943 | A2 | 9/1988 |
| EP | 0500437 | A1 | 8/1992 |
| EP | 0530974 | A1 | 3/1993 |
| EP | 0647617 | A1 | 4/1995 |
| EP | 1352629 | A1 | 10/2003 |
| EP | 1468667 | A1 | 10/2004 |
| FR | 2823110 | A1 | 10/2002 |
| FR | 2838336 | A1 | 10/2003 |
| FR | 2842200 | A1 | 1/2004 |
| FR | 2854161 | A1 | 10/2004 |
| FR | 2910275 | A1 | 6/2008 |
| FR | 2944438 | A1 | 10/2010 |
| FR | 2944967 | A1 | 11/2010 |
| FR | 2975593 | A1 | 11/2012 |
| WO | WO 2006057437 | A1 * | 6/2006 .............. A45D 2/48 |
| WO | 2007/090554 | A1 | 8/2007 |
| WO | 2009/150198 | A1 | 12/2009 |

OTHER PUBLICATIONS

International Search Report for PCT/EP2013/054720.
(Continued)

Primary Examiner — Nicole P Babson
(74) Attorney, Agent, or Firm — The Marbury Law Group, PLLC

(57) ABSTRACT

The present invention relates to a cosmetic treatment process for keratin fibers which have not been artificially colored, in particular human keratin fibers such as the hair, which consists in using one or more anionic oxidized polysaccharides and in raising the temperature of the keratin fibers.

11 Claims, No Drawings

(56) References Cited

FOREIGN PATENT DOCUMENTS

| WO | WO 2010070235 A2 * | 6/2010 | ............... A61K 8/73 |
|---|---|---|---|
| WO | 2011/161020 A1 | 12/2011 | |
| WO | 2015/036473 A1 | 3/2015 | |
| WO | 2015/036474 A1 | 3/2015 | |
| WO | 2015/036475 A1 | 3/2015 | |
| WO | 2015/036476 A1 | 3/2015 | |
| WO | 2015/036477 A1 | 3/2015 | |

OTHER PUBLICATIONS

Machine translated English language Abstract for FR 2842200.
English language Abstract for FR 2854161.
English language Abstract for FR 2944967.
International Search Report for counterpart Application No. PCT/EP2014/069377, dated Jan. 22, 2015.
International Search Report for counterpart Application No. PCT/EP2014/069378, dated Jan. 21, 2015.
International Search Report for counterpart Application No. PCT/EP2014/069380, dated Jan. 22, 2015.
International Search Report for counterpart Application No. PCT/EP2014/069381, dated Feb. 13, 2015.
International Search Report for counterpart Application No. PCT/EP2014/069383, dated Feb. 11, 2015.
First Office Action for counterpart Chinese Application No. 201480050160, dated Apr. 24, 2017.
Second Office Action for counterpart Chinese Application No. 201480050160, dated Nov. 27, 2017.
Non-Final Office Action for copending U.S. Appl. No. 15/021,402, dated Apr. 6, 2017.
Final Office Action for copending U.S. Appl. No. 15/021,402, dated Sep. 28, 2017.
Non-Final Office Action for copending U.S. Appl. No. 15/021,438, dated Jul. 18, 2017.
Final Office Action for copending U.S. Appl. No. 15/021,438, dated Dec. 28, 2017.
Non-Final Office Action for copending U.S. Appl. No. 15/021,452, dated Jul. 27, 2017.

* cited by examiner

PROCESS FOR PROTECTING AND REPAIRING KERATIN FIBRES USING ANIONIC OXIDIZED POLYSACCHARIDES

CROSS REFERENCE TO RELATED APPLICATIONS

This is a national stage application of PCT/EP2013/054720, filed internationally on Mar. 8, 2013, which claims priority to U.S. Provisional Application No. 61/642,602, filed on May 4, 2012, as well as French Application No. 1252149, filed Mar. 9, 2012, all of which are incorporated herein by their entireties.

The present invention relates to a cosmetic treatment process for keratin fibres which have not been artificially coloured, in particular human keratin fibres such as the hair, which consists in using one or more oxidized polysaccharides and in raising the temperature of the keratin fibres. The invention relates in particular to a process for protecting and repairing keratin fibres which have not been artificially coloured.

The hair is generally damaged and embrittled by the action of external atmospheric agents such as light and bad weather, and also by mechanical or chemical treatments, such as brushing, combing, dyeing, bleaching, permanent-waving and/or relaxing.

The hair is thus damaged by these various factors and may over time become dry, coarse, brittle or dull, in particular in fragile areas, and more particularly at the ends.

Thus, to overcome these drawbacks, it is common practice to resort to haircare products using compositions that condition the hair appropriately, giving it satisfactory cosmetic properties, in particular in terms of smoothness, sheen, softness, manageability, lightness, a natural feel and good disentangling properties. These compositions therefore have the objective of protecting, repairing and cosmetically transforming the hair in a long-lasting manner.

These haircare compositions may be, for example, conditioning shampoos, conditioners, masks or sera, and may be in the form of gels, hair lotions or care creams that are more or less thick.

It is known practice to use care compositions comprising reducing sugars, such as monosaccharides, used as conditioning agents, for in particular repairing keratin fibres that have been damaged by aggressive treatments.

Indeed, application US 2002/0193264 describes a process for conditioning keratin fibres, in which at least one sugar chosen from $C_3$-$C_5$ monosaccharides is applied to said fibres and a step of heating the keratin fibres is carried out.

Similarly, patent application US 2002/0172653 discloses a process for conditioning keratin fibres comprising a step of applying to said fibres a sugar chosen from specific $C_5$-$C_7$ monosaccharides and a step of heating the keratin fibres.

However, the use of reducing sugars followed by a heat treatment has the disadvantage of leading to an undesired modification of the colour of the keratin fibres.

Furthermore, reducing sugars degrade easily, in particular under the action of shampoos, which results in the cosmetic properties conferred on the fibres not being persistent. Thus, the keratin fibres are not protected, repaired or cosmetically transformed in a long-lasting manner.

Moreover, in the dyeing field, the use of one or more oxidized polysaccharides for protecting the colour of keratin fibres which have been artificially dyed, in particular by oxidation dyeing or direct dyeing, is known from patent application FR 2944967.

There is therefore a real need to carry out, on keratin fibres which have not been artificially coloured, a cosmetic treatment process which does not have the drawbacks of the existing processes, i.e. which is capable of conditioning keratin fibres in a long-lasting manner without causing a modification of their colour.

This objective is achieved by the present invention, a subject of which is in particular a cosmetic treatment process for keratin fibres which have not been artificially coloured, in particular human keratin fibres such as the hair, comprising:

(i) a step consisting in applying to said fibres a cosmetic composition comprising, in a cosmetically acceptable medium, one or more anionic oxidized polysaccharides, and (ii) a step consisting in heating the keratin fibres.

The treatment process according to the invention makes it possible to repair, protect and cosmetically transform the keratin fibres in a long-lasting manner without causing a modification of their colour. In other words, the oxidized polysaccharides in the presence of a heat treatment exhibit a repair, protection and cosmetic transformation activity on the fibres without resulting in a modification of the colour.

The process thus makes it possible to satisfactorily condition the keratin fibres.

In particular, the hair treated by means of the process according to the invention is softer to the touch and remains well-behaved since the presence of frizziness is not observed. Thus, the hair is aligned, straight and disentangles easily, which makes it easy to comb.

After treatment, the hair is not laden and has a natural and clean feel.

More particularly, the hair treated by means of the process according to the invention is structurally reinforced and is therefore less brittle and more resistant.

Moreover, the cosmetic properties conferred on the hair are persistent, in particular with respect to washing. Consequently, the hair can be protected, repaired and cosmetically transformed in a long-lasting manner.

Thus, the treatment process has the advantage of being able to be carried out as a pretreatment for a dyeing process, a relaxing process and/or a permanent-waving process in order to cosmetically protect the keratin fibres against these treatments. In other words, this process is performed in order to preserve the cosmetic properties of keratin fibres before a cosmetic treatment process as previously described.

The treatment process according to the invention may also be carried out as a post-treatment for a cosmetic treatment process which does not result in the keratin fibres being artificially coloured.

In particular, the treatment process is carried out as a post-treatment for a bleaching process, a relaxing process and/or a permanent-waving process in order to repair said fibres.

The process according to the invention also has the advantage of being able to be carried out during a cosmetic treatment process which does not result in the keratin fibres being artificially coloured, in order to repair said fibres.

The treatment process according to the invention does not cause any colouration of the hair, unlike an identical process using monosaccharides.

In addition, the deterioration of the surface condition of keratin fibres which is generally caused by heat, in particular in the case of the application of a straightening iron on the fibres, is much reduced with the oxidized polysaccharides as compared with the monosaccharides.

Furthermore, it has been observed that the treatment process according to the invention makes it possible to reinforce the cohesion inside the hair.

Other characteristics and advantages of the invention will emerge more clearly on reading the description and the examples that follow.

For the purposes of the present invention, the expression "keratin fibres which have not been artificially coloured" means keratin fibres which have not been dyed following a direct dyeing process or by an oxidation dyeing process.

In particular, the treatment process according to the invention can be carried out on damaged keratin fibres which have not been artificially coloured, such as bleached, relaxed or permanent-waved fibres.

In other words, the treatment process according to the invention is preferably carried out on sensitized keratin fibres which have not been artificially coloured.

For the purposes of the present invention, the term "washing" means one or more applications to the keratin fibres of an aqueous rinse-out composition, which is usually a detergent composition such as a shampoo.

The oxidized polysaccharide(s) is (are) anionic.

The anionic oxidized polysaccharides are constituted of monosaccharide units which can comprise five carbon atoms or more, preferably six carbon atoms or more, and more particularly six carbon atoms.

The anionic oxidized polysaccharides comprise one or more aldehydes and one or more anionic groups.

These anionic groups are preferably carboxyl or carboxylate groups.

The anionic oxidized polysaccharides according to the invention can be represented by formula (I) below:

$$P\text{---}(CHO)_m(COOX)_n \qquad (I)$$

in which:

P represents a polysaccharide chain constituted of monosaccharides comprising 5 carbon atoms or more than 5 carbon atoms, preferably 6 or more than 6 carbon atoms and more particularly 6 carbon atoms, X is chosen from a hydrogen atom, the ions derived from an alkali metal or an alkaline-earth metal such as sodium or potassium, aqueous ammonia, organic amines such as monoethanolamine, diethanolamine, triethanolamine and 3-amino-1,2-propanediol and basic amino acids such as lysine, arginine, sarcosine, ornithine and citrulline, m+n is greater than or equal to 1, m is such that the degree of substitution of the polysaccharide with one or more aldehyde groups (DS(CHO)) is included in the range of from 0.001 to 2 and preferably from 0.005 to 1.5, n is such that the degree of substitution of the polysaccharide with one or more carboxylic groups (DS(COOX)) is included in the range of from 0.001 to 2 and preferably from 0.001 to 1.5.

The term "degree of substitution DS(CHO) or DS(COOX) of the polysaccharides according to the invention" means the ratio between the number of carbons oxidized as an aldehyde or carboxylic group for all the repeating units and the number of elemental monosaccharides (even opened by preoxidation) constituting the polysaccharide.

The CHO and COOX groups can be obtained during the oxidation of certain carbon atoms, for example in the $C_2$, $C_3$ or $C_6$ position, of a saccharide unit comprising 6 carbon atoms; preferably, the oxidation can take place at $C_2$ and at $C_3$, more particularly from 0.01% to 75% by number and preferably from 0.1% to 50% by number of the rings having possibly been opened.

The polysaccharide chain, represented by P, is preferably chosen from inulins, celluloses, starches, guar gums, xanthan gums, pullulan gums, alginate gums, agar-agar gums, carrageenan gums, gellan gums, gums arabic, xyloses and tragacanth gums, and derivatives thereof, cellobiose, maltodextrin, scleroglucan, chitosan, ulvan, fucoidan, alginate, pectin, heparin, hyaluronic acid or mixtures thereof.

More preferentially, the polysaccharide chain is chosen from inulins or starches.

Even more preferentially, the polysaccharide chain is inulin.

The term "derivative" means the compounds obtained by chemical modification of the mentioned compounds. They may be esters, amides or ethers of said compounds.

The oxidation may take place according to a process known in the art, for example according to the process described in FR 2 842 200, in document FR 2 854 161 or in the article "Hydrophobic films from maize bran hemicelluloses" by E. Fredon et al., Carbohydrate Polymers 49, 2002, pages 1 to 12. Another oxidation process is described in the article "Water soluble oxidized starches by peroxide reaction extrusion", Industrial Crops and Products 75 (1997) 45-52-R. E. Wing, J. L. Willet. These oxidation processes are simple to carry out, are efficient and do not generate any toxic by-products or by-products that are difficult to eliminate.

The peroxides that may be used during these oxidation processes may be an alkali metal or alkaline-earth metal percarbonate or perborate, an alkyl peroxide, peracetic acid or hydrogen peroxide. Hydrogen peroxide is particularly preferred, since it is readily accessible and it does not produce any bothersome by-products.

The amount of peroxide in the reaction medium is between 0.05 and 1 molar equivalent per glucose unit of the polysaccharide and preferably between 0.1 and 0.8 molar equivalent. It is preferable to add the peroxide in successive fractions, while leaving the reaction medium to stir between two additions.

A single phthalocyanin or a mixture of phthalocyanins, for example a mixture of cobalt phthalocyanin and of iron phthalocyanin, may be used as catalyst during the oxidation process. The amount of catalyst depends on the desired degree of substitution. In general, a small amount, for example an amount corresponding to 0.003 to 0.016 molar equivalent per 100 glucose units of polysaccharide, is suitable.

The process may also be carried out by bringing the polysaccharide in pulverulent form into contact with the catalyst dissolved in a small volume of water and with the peroxide. This process is referred to as a "semi-dry" process.

The process may be carried out by reactive extrusion in the presence of peroxide.

More preferentially, the polysaccharide is obtained by oxidation of inulin, cellulose, carboxymethylcellulose, hydroxyethylcellulose, hydroxypropylcellulose, hydroxypropylmethylcellulose, methylcellulose, starch, starch acetate, hydroxyethyl starch, hydroxypropyl starch, guar gum, carboxymethyl guar gum, carboxymethylhydroxypropyl guar gum, hydroxyethyl guar gum, hydroxypropyl guar gum, xylose, xanthan gum, carrageenan gum, cellobiose, maltodextrin, scleroglucan, chitosan, ulvan, fucoidan, alginate, pectin, heparin and hyaluronic acid, or mixtures thereof.

Preferentially, the polysaccharide is obtained by oxidation of inulin or of starch.

Preferentially, the polysaccharide is obtained by oxidation of inulin.

According to one embodiment, the polysaccharide is obtained by oxidation of inulin by carrying out a reactive extrusion process in the presence of hydrogen peroxide.

The polysaccharide chain before and after oxidation preferably has a weight-average molecular weight ranging from 400 to 15 000 000, even better still from 500 to 10 000 000 and more particularly from 500 to 50 000 g/mol.

The polysaccharides that are most particularly preferred in the invention are those corresponding to formula (I) in which: P represents a polymer chain derived from inulin or from starch, m is such that the degree of substitution of the polysaccharide with one or more aldehyde groups (DS(CHO)) is included in the range of from 0.005 to 2.5, and n is such that the degree of substitution of the polysaccharide with one or more carboxylic groups (DS(COOX)) is included in the range of from 0.001 to 2.

Even more preferably, P represents a polymer chain derived from inulin, m is such that the degree of substitution of the polysaccharide with one or more aldehyde groups (DS(CHO)) is included in the range of from 0.01 to 1, and n is such that the degree of substitution of the polysaccharide with one or more carboxylic groups (DS(COOX)) is included in the range of from 0.01 to 2.

The oxidized polysaccharide(s) may be present in the cosmetic composition in a content ranging from 0.01% to 10% by weight and preferably in a content ranging from 0.5% to 5% by weight, relative to the total weight of the composition.

The cosmetically acceptable medium of the compositions in accordance with the invention can, for example, be constituted of water or of a mixture of water and at least one cosmetically acceptable organic solvent. Examples of organic solvents that may be mentioned include $C_1$-$C_4$ lower alcohols, such as ethanol and isopropanol; polyols and polyol ethers, for instance 2-butoxyethanol, propylene glycol, propylene glycol monomethyl ether, diethylene glycol monoethyl ether and monomethyl ether, and mixtures thereof.

Preferably, the cosmetic composition comprises from 50% to 99.5% by weight of water relative to the weight of the composition comprising the oxidized polysaccharides.

The pH of the compositions according to the invention is generally between 2 and 11, preferably between 3 and 10 and even better still between 4 and 8. The pH is adapted by using additional acidifying or basifying agents, such as those mentioned below.

Among the additional acidifying agents that may be mentioned, for example, are inorganic or organic acids, for instance hydrochloric acid, orthophosphoric acid or sulfuric acid, carboxylic acids, for instance acetic acid, tartaric acid, citric acid and lactic acid, and sulfonic acids.

As regards the additional basifying agent, if it is present, it may be chosen from non-salified organic amines comprising a primary, secondary or tertiary amine function, and one or more linear or branched $C_1$-$C_8$ alkyl groups bearing one or more hydroxyl radicals.

Organic amines chosen from alkanolamines such as monoalkanolamines, dialkanolamines or trialkanolamines comprising one to three identical or different $C_1$-$C_4$ hydroxyalkyl radicals are in particular suitable.

Among compounds of this type, mention may be made of monoethanolamine, diethanolamine, triethanolamine, mono isopropanolamine, diisopropanolamine, N-dimethylamin- oethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

Also suitable are the organic amines having the following formula:

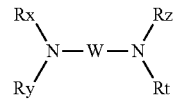

in which W is a $C_1$-$C_6$ alkylene residue optionally substituted with a hydroxyl group or a $C_1$-$C_6$ alkyl radical; Rx, Ry, Rz and Rt, which may be identical or different, represent a hydrogen atom or a $C_1$-$C_6$ alkyl, $C_1$-$C_6$ hydroxyalkyl or $C_1$-$C_6$ aminoalkyl radical.

The composition according to the invention may also comprise one or more additives chosen from anionic polymers different from the polysaccharides of the invention, non-ionic polymers different from the polysaccharides of the invention, cationic polymers or amphoteric polymers, linear, branched or cyclic silicones which are volatile or non-volatile and organo modified or non-organo modified, foam synergists such as $C_{10}$-$C_{18}$ 1,2-alkane diols or fatty alkanolamides derived from $C_8$-$C_{24}$ fatty acid monoethanolamine or diethanolamine, nacreous agents, opacifiers, dyes or pigments, fragrances, mineral, vegetable or synthetic oils, waxes, $C_8$-$C_{50}$ fatty alcohols, oxyalkylenated fatty alcohols, vitamins, provitamins, UV screening agents, free-radical scavengers, antidandruff agents, antiseborrhoeic agents, anti-hairloss agents, preservatives, pH stabilizers, and mixtures thereof and any other additive conventionally used in the cosmetics field.

Preferably, the composition according to the invention may also comprise one or more additives chosen from silicones, oils and cosmetically acceptable solvents.

The compositions in accordance with the invention may contain, in addition to the combination defined above, viscosity regulators.

Those skilled in the art will take care to select the optional additives and the amount thereof such that they do not harm the properties of the compositions of the present invention.

The compositions according to the invention are preferably liquid, i.e. have a viscosity ranging from 10 to 6000 cps measured at 25° C. with a Rheomat RM 180 viscometer at a shear rate of 100 s$^{-1}$. These compositions may be in the form of optionally thickened lotions, of creams, of mousses or of a gel. The compositions may be packaged in various forms, in particular in bottles, in pump-dispenser bottles or in aerosol containers so as to apply the composition in vaporized form or in the form of a mousse.

As previously indicated, the treatment process according to the invention comprises a step of heating the keratin fibres.

The step of heating the keratin fibres can be carried out at a temperature ranging from 45° C. to 250° C. and more particularly at a temperature ranging from 80° C. to 180° C., in particular 180° C.

The heating step can, during all or part of the time, be carried out using any device that produces heat and in particular by means of a hairstyling hood, a hairdryer, a straightening or curling iron or an infrared ray dispenser.

When it is desired to work at low temperatures ranging from 50 to 75° C. in order to carry out gentle heating, the composition comprising one or more anionic oxidized polysaccharides is applied to wet hair, which is then left to dry under a hood at temperatures ranging from 50 to 75° C. and the heat is maintained for 15 to 30 minutes, for example.

When it is desired to work at high temperatures in order to carry out stronger heating, the composition comprising one or more anionic oxidized polysaccharides is applied to wet hair, the hair is left to dry under a hood or at ambient temperature, the hair is combed, and then the straightening iron is applied by performing several continuous passes along the locks for 40 seconds.

Preferably, the step of heating the keratin fibres is carried out by means of a straightening iron at a temperature which can range from 80 to 180° C.

Preferably, the heating step can consist in leaving the hair under a hood at a temperature ranging from 50 to 75° C. and in then applying the straightening iron at a temperature ranging from 80 to 180° C.

According to one embodiment, the treatment process according to the invention comprises a first step in which a composition comprising, in a cosmetically acceptable medium, one or more anionic oxidized polysaccharides is applied to the keratin fibres and a second step in which said fibres are heated, preferentially at a temperature ranging from 45° C. to 250° C. and in particular at a temperature ranging from 70° C. to 180° C., such as 80° C.

According to another embodiment, the treatment process according to the invention comprises a first step in which a composition comprising, in a cosmetically acceptable medium, one or more anionic oxidized polysaccharides is applied to the keratin fibres, a second step in which the fibres are rinsed with water and then a third step in which said fibres are heated, preferentially at a temperature ranging from 45° C. to 250° C. and in particular at a temperature ranging from 100° C. to 180° C.

The keratin fibres can then be rinsed with water and/or washed and air-dried or dried with a drying means.

Preferably, the step of heating the keratin fibres is carried out by means of a straightening iron at a temperature of 180° C.

The treatment process according to the invention can be carried out at the same time as the shaping under mechanical tension of the keratin fibres.

This placing under mechanical tension can be carried out, for example, by means of curlers, a curling iron, a steam iron or a straightening iron:
(a) before during the application of a composition comprising the oxidized polysaccharide(s), and
(b) before the step of heating the keratin fibres.

According to one particular embodiment, the hair may be wetted beforehand and is rolled onto tensioning means such as rollers. Said rollers preferentially have a diameter of from 2 to 30 mm. The compound(s) of formula (I) can also be applied as the hair is rolled or else be impregnated in the curlers when they are, for example made of foam.

The step of placing the keratin fibres under tension may be carried out via any means, for example with elastic bands, clips, combs, hair slides or hair ties, or alternatively with conventional cylindrical curlers or rollers, and curlers of "tulip" type. The curlers may be made of foam, such as, for example, those described in document U.S. Pat. No. 5,992, 425. In this case, the foam roller can be impregnated with a hair product such as the cosmetic composition comprising at least one polymer of formula (I) as previously defined and onto which the lock of keratin fibres is wound with the aim of coating this lock with product over its entire wound length. "Tulip" curlers are made up of an elongated stem, and the tensioning means are curlers 2 to 30 mm in diameter.

Preferably, the treatment process can be carried out before, during and/or after a cosmetic treatment process for keratin fibres.

In particular, the treatment process can be carried out before a process for dyeing, a process for relaxing and/or a process for permanent-waving keratin fibres.

As a variant, the treatment process can be carried out during and/or after a cosmetic treatment process which does not result in the artificial colouration of the keratin fibres, in particular:
(a) during and/or after a process for permanent-waving or a process for relaxing keratin fibres, and
(b) after a process for bleaching keratin fibres.

Preferably, the treatment process is carried out during a cosmetic treatment process which does not result in the artificial colouration of the keratin fibres.

According to one embodiment, the treatment process according to the invention is carried out after a process for bleaching keratin fibres.

The process for bleaching keratin fibres can be carried out by applying to said fibres a composition which may comprise one or more oxidizing agents chosen from hydrogen peroxide, urea peroxide, alkali metal bromates, persalts such as perborates and persulfates, and enzymes such as peroxidases and two-electron or four-electron oxidoreductases. The use of hydrogen peroxide is particularly preferred.

The content of oxidizing agent in the composition can be between 0.1% and 10% by weight of the composition and preferably between 0.5% and 6% by weight relative to the total weight of the composition.

Preferably, the pH of the composition after mixing with the oxidizing agent is between 5 and 10.5 and preferably between 6 and 10.

The composition can comprise an alkaline agent, such as sodium hydroxide, potassium hydroxide, aqueous ammonia, amines or alkanolamines.

According to another embodiment, the treatment process according to the invention is carried out before, during or after a process for permanently reshaping keratin fibres.

The permanently reshaping process consists in carrying out the following steps:
(i) a reducing composition comprising, in a cosmetically acceptable medium, one or more reducing agents is applied to the keratin fibres and is left on for the time sufficient for shaping, and
(ii) an oxidizing composition is applied for a time sufficient for fixing the shape.

The reducing agents used during step (i) of the permanently reshaping process may be chosen from thiols such as thioglycolic acid and thiolactic acid, salts thereof and esters thereof, cysteine, cysteamine and derivatives thereof, sulfites and bisulfites, in particular of alkali metals, of alkaline-earth metals or of ammonium, and mixtures thereof.

More preferentially, the thiolated reducing agents are thioglycolic acid and thiolactic acid or salts thereof and even more preferentially thioglycolic acid.

The reducing agents may be present in the reducing composition in a content ranging from 0.1% to 20% by weight and preferably in a content ranging from 0.5% to 15% by weight, relative to the total weight of the reducing composition.

Generally, the medium of this composition comprises water or a mixture of water and one or more cosmetically acceptable solvents. The cosmetically acceptable solvents that may be used in the reducing composition may correspond to those used in the case of the dye composition.

The solvent content is more particularly not more than 20% by weight relative to the total weight of the reducing composition.

The reducing composition may also comprise common additives such as non-ionic, anionic, cationic or amphoteric surfactants, and, among these, mention may be made of alkyl sulfates, alkylbenzene sulfates, alkyl ether sulfates, alkylsulfonates, quaternary ammonium salts, alkylbetaines, oxyethylenated alkylphenols, fatty acid alkanolamides, oxyethylenated fatty acid esters, and also other non-ionic surfactants of the hydroxypropyl ether type.

When the reducing composition contains this type of additive, its content is generally less than 30% by weight and preferably between 0.5% and 10% by weight relative to the total weight of the reducing composition.

The reducing composition may be in the form of a thickened or unthickened lotion, a cream or a gel, or in any other suitable form.

The leave-on time is generally between 3 and 30 minutes and preferably between 5 and 15 minutes.

The oxidizing composition used in step (ii) of the permanently reshaping process conventionally comprises one or more oxidizing agents, in general aqueous hydrogen peroxide solution, an alkali metal bromate, a persalt or a polythionate, and even more preferentially aqueous hydrogen peroxide solution.

The pH of the oxidizing composition is generally between 2 and 10.

The leave-on time is generally between 3 and 30 minutes and preferably between 5 and 15 minutes.

More preferentially, the treatment process according to the invention is carried out during a process for permanently reshaping keratin fibres.

According to one particular embodiment, the reducing composition is applied in order to reduce the keratin disulfide bonds, the keratin fibres being placed under mechanical tension before, during or after said application, and the reducing composition is then left to act for a time generally of from 5 to 60 minutes and preferably for from 5 to 30 minutes.

The cosmetic composition comprising one or more anionic oxidized polysaccharides is then applied to said keratin fibres.

The head of hair is then subjected to a heat treatment by heating at a temperature which can range from 45 to 250° C. and preferably from 80 to 180° C., for all part of the leave-on time. In practice, this operation may be performed using a hairstyling hood, a hairdryer, a round or flat iron, an infrared ray dispenser or other standard heating appliances.

Use may in particular be made, both as a means for heating and as a means for shaping the head of hair, of an iron heating at a temperature ranging from 45 to 250° C. and preferably from 80 to 180° C.

The oxidizing composition for reforming the keratin disulfide bonds is then applied to the rolled up or unrolled hair, generally for a leave-on time of from 2 to 15 minutes.

When it is desired to perform permanent waving, mechanical means are preferably used, such as curlers, in order to place the keratin fibres under tension, the reducing composition being applied before, during or after the hair-shaping means, preferably after.

In the case of a hair relaxing or straightening process, the reducing composition is applied to the hair, and the hair is then subjected to mechanical reshaping for fixing the hair in its new shape, by means of a hair straightening operation, with a large-toothed comb, with the back of a comb, by hand or with a brush. A leave-on time of from 5 to 60 minutes and preferably from 15 to 45 minutes is generally implemented.

The straightening of the hair may also be performed, totally or partly, using a straightening iron heating at between 60 and 220° C. and preferably between 120 and 200° C.

As a variant, the permanently reshaping process may be a process for permanently reshaping by straightening or relaxing, carried out following the application of an alkaline cosmetic composition with a pH of at least 10, comprising one or more alkaline agents.

In particular, an alkaline cosmetic composition with a pH of greater than or equal to 10 comprising, in a cosmetically acceptable medium, one or more alkaline agents is applied to the keratin fibres while straightening them, and is left on for the time sufficient for shaping.

The alkaline agent(s) is (are) chosen from alkaline agents of inorganic or organic hydroxide type, in an amount such that the pH of the composition is at least greater than 10, preferably between 10 and 14 and better still between 12 and 14.

More particularly, the alkaline agent of hydroxide type is chosen from hydroxides of alkali metals or alkaline-earth metals, of transition metals, in particular of groups IIIB, IVB, VB and VIB, of lanthanides or of actinides, ammonium hydroxides and guanidine hydroxide, or mixtures thereof.

By way of examples of such compounds, mention may be made of sodium hydroxide, potassium hydroxide, lithium hydroxide, rubidium hydroxide, caesium hydroxide, francium hydroxide, magnesium hydroxide, calcium hydroxide, strontium hydroxide, barium hydroxide, manganese hydroxide, zinc hydroxide, cerium hydroxide, lanthanum hydroxide, actinium hydroxide, thorium hydroxide, aluminium hydroxide, guanidine hydroxide and quaternary ammonium hydroxides.

It should be noted that certain hydroxides, and more particularly guanidine hydroxide, may be in the form of precursors, i.e. of at least two compounds which, when placed in contact, produce guanidine hydroxide via a chemical reaction. By way of example, mention may thus be made of the combination of an alkaline-earth metal hydroxide, for instance calcium hydroxide, with guanidine carbonate.

Advantageously, the amount of alkaline agent of hydroxide type is between 0.5% and 10% by weight and preferably between 1% and 8% by weight relative to the weight of the composition.

In particular, the cosmetic treatment process according to the invention is a process for protecting and/or repairing keratin fibres which have not been artificially coloured, comprising:

(i) a step of applying to said fibres a cosmetic composition comprising, in a cosmetically acceptable medium, one or more anionic oxidized polysaccharides, and (ii) a step of heating the keratin fibres.

The following examples are given as illustrations of the present invention.

EXAMPLES

Part A

The amounts indicated in the examples are expressed as weight percentages.

I. Oxidized Polysaccharide Tested

Compound 1 was prepared by oxidation of inulin sold under the name Inutec N25 by the company Orafti, by carrying out a reactive extrusion process as described in the article "Water soluble oxidized starches by peroxide reactive extrusion" by R. E. Wing and J. L. Willett, Industrial Crops and Products 7, 1997, pages 45-52. A co-rotating twin-screw extruder of BC21 type sold by the company Clextral and aqueous hydrogen peroxide solution, as oxidizing agent, were used.

Compound 1: oxidized inulin obtained by reactive extrusion of a mixture of 78% by weight of inulin and 1.57% by weight of aqueous hydrogen peroxide solution, in water; the spontaneous pH after reactive extrusion is 3.8. The resulting compound 1 has a carbonyl content of 1.23% (w/w) and a carboxyl content of 0.17% (w/w).

Compositions Tested

|  | Compositions | | | |
| --- | --- | --- | --- | --- |
|  | A | B | C | D |
| Compound 1 | 0.5% | 2% | — | — |
| Acidifying agent | — | — | — | qs pH = 3 |
| Water | qs 100 | qs 100 | qs 100 | qs 100 |

The pH of compositions (A), (B) and (C) is about 3.4.

III. Procedure

Each of the compositions is applied to locks of highly sensitized hair (SA=45%), in a proportion of 10 ml of composition per gram of lock, for 30 minutes at 40° C.

The locks are then wrung out and are then dried under a hood for 10 minutes at 60° C.

The locks are combed before applying a straightening iron at a temperature of 180° C., making five continuous passes along the locks for 40 seconds.

IV. Results—Cosmetic Properties

The cosmetic properties of the locks of hair are observed and evaluated following treatment carried out with each of the compositions (A) to (D) after shampooing.

The cosmetic feel and the manageability of the locks, and the ease with which they can be combed, are in particular evaluated.

| Type of hair lock | Cosmetic properties after shampooing |
| --- | --- |
| Untreated sensitized hair (control) (Lock 1) | Difficult to comb |
| Sensitized hair treated with composition (C) + heat (Lock 2) | Difficult to comb, same level as lock 1 |
| Sensitized hair treated with composition (D) + heat (Lock 3) | Slightly well-behaved lock easier to comb than lock 1 |
| Sensitized hair treated with composition (A) + heat (Lock 4) | Lock easy to comb, well-behaved and pleasant and soft cosmetic feel |
| Sensitized hair treated with composition (B) + heat (Lock 5) | Lock easy to comb, well-behaved and pleasant feel |

The locks of hair were then classified according to their cosmetic properties (soft and pleasant cosmetic feel, manageability, ease of combing and resistance) after shampooing.

| After shampooing | Lock No. 4 > Lock No. 5 > Lock No. 6 > Lock No. 3 > Lock No. 2 > Lock No. 1 |
| --- | --- |

The locks treated by means of the process according to the invention have better cosmetic properties after shampooing.

The persistence of the cosmetic properties is therefore improved.

V. Colorimetric Measurements 5.1 The colour of the locks of hair is evaluated before and after the treatment previously described for each of compositions (A) to (D) (procedure—part III) in the CIE L*a*b* system, using a Konica-Minolta CM2600D colorimeter (specular components included, illuminant D65, angle 10°).

The variation in colouration DE of the locks of hair before and after treatment is calculated on the basis of the values L*a*b* measured before and after treatment and is obtained from the following equation:

$$DE = \sqrt{(L^*-L_0^*)^2+(a^*-a_0)^2+(b^*-b_0^*)^2} \quad (i)$$

In this equation, L*, a* and b* represent the values measured on the untreated sensitized locks of hair and $L_0^*$, $a_0^*$ and $b_0^*$ represent the values measured on the sensitized locks of hair after the treatment was carried out for each of compositions (A) to (D).

VI. Results

| Type of lock | L* | a* | b* | DE |
| --- | --- | --- | --- | --- |
| Untreated sensitized hair (control) (Lock 1) | 68.59 ± 1.5 | 4.64 ± 0.69 | 28.47 ± 1.28 | — |
| Sensitized hair treated with composition (C) + heat (Lock 2) | 67.25 ± 1.03 | 5.02 ± 0.5 | 27.84 ± 1.04 | 1.53 ± 1.17 |
| Sensitized hair treated with composition (D) + heat (Lock 3) | 67.55 ± 1.66 | 5.29 ± 0.50 | 28.06 ± 1.19 | 1.30 ± 1.19 |
| Sensitized hair treated with composition (A) + heat (Lock 4) | 68.74 ± 1.22 | 4.59 ± 0.55 | 26.29 ± 0.91 | 2.19 ± 1.19 |
| Sensitized hair treated with composition (B) + heat (Lock 5) | 66.90 ± 1.85 | 4.32± 0.76 | 26.61 ± 1.33 | 2.53 ± 1.43 |

The locks of hair treated by means of the treatment process according to the invention do not undergo any colour modification.

VII. Evaluation of the Dry Friction Properties 7.1 Procedure

The measurements of the friction coefficient of the hair are determined using a friction bench constituted of a glass plate with two pierced Teflon end pieces for threading through two hairs.

An 11.0 gram stainless steel sled is adjusted on the plate, the scan speed is 20 Hz/second and the translation speed is 2.0 rpm. The measurements are carried out in both directions of the fibre (root to end and end to root) at a temperature of 25° C. and a relative hygrometry of 45%.

7.2 Results

| Type of lock | Dynamic friction coefficient of the hair root-end |
| --- | --- |
| Untreated sensitized hair (control) (Lock 1) | 0.133 ± 0.042 |

| Type of lock | Dynamic friction coefficient of the hair root-end |
|---|---|
| Sensitized hair treated with composition (C) + heat (Lock 2) | 0.166 ± 0.052 |
| Sensitized hair treated with composition (D) + heat (Lock 3) | 0.159 ± 0.045 |
| Sensitized hair treated with composition (A) + heat (Lock 4) | 0.131 ± 0.022 |
| Sensitized hair treated with composition (B) + heat (Lock 5) | 0.118 ± 0.024 |

It is noted that the treatment process according to the invention makes it possible to further reduce the dry friction coefficient of the hair.

It is noted that this decrease in the friction coefficient increases with the concentration of the polysaccharide.

Part B

The amounts indicated in the compositions described hereinafter are expressed as weight percentages.

I. Oxidized Polysaccharide Tested

Compound 1 was prepared by oxidation of inulin sold under the name Inutec N25 by the company Orafti in the same way as in part A (Part A.I).

Compositions Tested

| | Compositions | | |
|---|---|---|---|
| | C | E | F |
| Compound 1 | — | 5% | — |
| Fructose | — | — | 5% |
| Water | qs 100 | qs 100 | qs 100 |

The pH of compositions (C), (E) and (F) is about C=7; E=3.02; F=6.33

III. Procedure

The procedure is identical to that carried out in part A (Part A.III).

IV. Colorimetric Measurements

The colour of the locks of hair is evaluated before and after the treatment previously described for each of compositions (C) to (F) (procedure—part III) in the CIE L*a*b* system, using a Konica-Minolta CM2600D colorimeter (specular components included, illuminant D65, angle 10°).

The variation in colouration DE of the locks of hair before and after treatment is calculated on the basis of the values L*a*b* measured before and after treatment and is obtained from the equation (i) previously described.

V. Results

| Type of lock | L* | a* | b* | DE |
|---|---|---|---|---|
| Untreated sensitized hair (control) (Lock 1') | 68.41 | 4.74 | 28.88 | — |
| Sensitized hair with composition (C) + heat (Lock 2') | 66.93 | 4.60 | 27.18 | 2.26 ± 1.21 |
| Sensitized hair treated with composition (E) + heat (Lock 3') | 66.89 | 5.53 | 28.72 | 1.10 ± 1.76 |
| Sensitized hair treated with composition (F) + heat (Lock 4') | 64.42 | 10.29 | 36.44 | 11.16 ± 1.23 |

The locks of hair treated with the process according to the invention (lock 3') do not undergo any colour modification, whereas the locks of hair treated with fructose (lock 4') undergo a considerable modification of their colour.

The invention claimed is:

1. A process for treating keratin fibers, the process comprising:
   (i) applying to said fibers a cosmetic composition comprising, in a cosmetically acceptable medium, at least one anionic oxidized polysaccharide chosen from compounds of formula (I) below:

$$P(CHO)_m(COOX)_n \qquad (I)$$

wherein:
   P represents a polysaccharide chain chosen from inulins;
   X is chosen from a hydrogen atom, ions derived from an alkali metal or an alkaline-earth metal, aqueous ammonia, organic amines, and basic amino acids;
   m+n is greater than or equal to 1;
   m is chosen such that the degree of substitution of the at least one polysaccharide with the at least one aldehyde group (DS(CHO)) ranges from about 0.001 to about 2; and
   n is chosen such that the degree of substitution of the at least one polysaccharide with the at least one carboxylic group (DS(COOX)) ranges from about 0.001 to about 2, and
   (ii) heating the keratin fibers using a straightening iron at a temperature ranging from about 80° C. to about 180° C.,
   wherein said keratin fibers have not been artificially colored prior to said treatment process.

2. The process according to claim 1, wherein:
   the alkali metal or an alkaline-earth metal is chosen from sodium, potassium, and mixtures thereof;
   the organic amines are chosen from monoethanolamine, diethanolamine, triethanolamine, 3-amino-1,2-propanediol, and mixtures thereof; and/or
   the basic amino acids are chosen from lysine, arginine, sarcosine, ornithine, citrulline, and mixtures thereof.

3. The process according to claim 1, wherein:
   m is chosen such that the degree of substitution of the at least one polysaccharide with the at least one aldehyde group (DS(CHO)) ranges from about 0.005 to about 1.5; and/or
   n is chosen such that the degree of substitution of the at least one polysaccharide with the at least one carboxylic group (DS(COOX)) ranges from about 0.001 to about 1.5.

4. The process according to claim 1, wherein the process is carried out on sensitized keratin fibers that have not been artificially colored prior to said treatment process.

5. The process according to claim 1, further comprising a step of cosmetically treating keratin fibers.

6. The process according to claim 5, wherein the cosmetic treatment process is chosen from dyeing, relaxing and/or permanent-waving keratin fibers.

7. The process according to claim 5, wherein the process is carried out during and/or after a cosmetic treatment process which does not result in the artificial coloration of the keratin fibers.

8. The process according to claim 1, wherein the process is carried out during and/or after a process for permanent-waving or a process for relaxing keratin fibers; or after a process for bleaching keratin fibers.

9. The process according to claim 1, wherein the process is carried out during a process for permanently reshaping keratin fibers.

10. A process for repairing keratin fibers, the process comprising:
applying to said fibers a cosmetic composition comprising, in a cosmetically acceptable medium, at least one anionic oxidized polysaccharide chosen from compounds of formula (I) below:

$$P\text{---}(CHO)_m(COOX)_n \qquad (I)$$

wherein:
P represents a polysaccharide chain chosen from inulins;
X is chosen from a hydrogen atom, ions derived from an alkali metal or an alkaline-earth metal, aqueous ammonia, organic amines, and basic amino acids;
m+n is greater than or equal to 1;
m is chosen such that the degree of substitution of the at least one polysaccharide with the at least one aldehyde group (DS(CHO)) ranges from about 0.001 to about 2; and
n is chosen such that the degree of substitution of the at least one polysaccharide with the at least one carboxylic group (DS(COOX)) ranges from about 0.001 to about 2, and (ii) heating the keratin fibers using a straightening iron at a temperature ranging from about 80° C. to about 180° C.,
wherein said keratin fibers have not been artificially colored prior to said repairing process.

11. A process for protecting keratin fibers, the process comprising:
applying to said fibers a cosmetic composition comprising, in a cosmetically acceptable medium, at least one anionic oxidized polysaccharide chosen from compounds of formula (I) below:

$$P\text{---}(CHO)_m(COOX)_n \qquad (I)$$

wherein:
P represents a polysaccharide chain chosen from inulins;
X is chosen from a hydrogen atom, ions derived from an alkali metal or an alkaline-earth metal, aqueous ammonia, organic amines, and basic amino acids;
m+n is greater than or equal to 1;
m is chosen such that the degree of substitution of the at least one polysaccharide with the at least one aldehyde group (DS(CHO)) ranges from about 0.001 to about 2; and
n is chosen such that the degree of substitution of the at least one polysaccharide with the at least one carboxylic group (DS(COOX)) ranges from about 0.001 to about 2, and
(ii) heating the keratin fibers using a straightening iron at a temperature ranging from about 80° C. to about 180° C.,
wherein said keratin fibers have not been artificially colored prior to said protecting process.

* * * * *

UNITED STATES PATENT AND TRADEMARK OFFICE
CERTIFICATE OF CORRECTION

PATENT NO. : 10,085,931 B2  
APPLICATION NO. : 14/383993  
DATED : October 2, 2018  
INVENTOR(S) : Baghdadli et al.

Page 1 of 1

It is certified that error appears in the above-identified patent and that said Letters Patent is hereby corrected as shown below:

In the Claims

Claim 1, Column 14, Line 22, change "P(CHO)" to -- P-(CHO) --.

Signed and Sealed this  
Sixth Day of November, 2018

Andrei Iancu  
*Director of the United States Patent and Trademark Office*